(12) United States Patent
Ritland

(10) Patent No.: US 8,845,694 B2
(45) Date of Patent: Sep. 30, 2014

(54) ROD EXTENSION FOR EXTENDING FUSION CONSTRUCT

(75) Inventor: Stephen Ritland, Flagstaff, AZ (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 0 days.

(21) Appl. No.: 13/236,200

(22) Filed: Sep. 19, 2011

(65) Prior Publication Data
US 2012/0010664 A1  Jan. 12, 2012

Related U.S. Application Data

(62) Division of application No. 11/458,629, filed on Jul. 19, 2006, now Pat. No. 8,021,399.

(60) Provisional application No. 60/700,887, filed on Jul. 19, 2005.

(51) Int. Cl.
 *A61B 17/70* (2006.01)
 *A61B 17/88* (2006.01)

(52) U.S. Cl.
 CPC ........... *A61B 17/7011* (2013.01); *A61B 17/705* (2013.01)
 USPC ............................ 606/277; 606/278; 606/279

(58) Field of Classification Search
 USPC .................................................. 606/277–279
 See application file for complete search history.

(56) References Cited

U.S. PATENT DOCUMENTS

| | | | |
|---|---|---|---|
| 2,191 A | 7/1841 | Pitney | |
| 569,839 A | 10/1896 | Roeloffs | |
| 605,652 A | 6/1898 | Pitt | |
| 1,090,746 A | 3/1914 | Nourse | |
| 1,097,978 A | 5/1914 | Johnson | |
| 2,611,434 A | 9/1952 | Mugler | |
| 3,467,079 A | 9/1969 | James | |
| 3,470,872 A | 10/1969 | Grieshaber | |
| 3,875,595 A | 4/1975 | Froning | |
| 3,893,454 A | 7/1975 | Hagelin | |

(Continued)

FOREIGN PATENT DOCUMENTS

| CA | 2320821 | 8/1999 |
|---|---|---|
| DE | 9004960 | 8/1991 |

(Continued)

OTHER PUBLICATIONS

Reissue U.S. Appl. No. 10/165,991 to Simonson, filed Jun. 10, 2002.

(Continued)

*Primary Examiner* — David Bates

(57) ABSTRACT

In accordance with embodiments of the present invention, a rod extension for extending a fusion construct is provided. The rod extension allows a surgeon to connect a stabilization rod implant to at least a portion of a patient's spine, and also to connect the stabilization rod implant to an existing implant that has been previously installed in the patient. The existing fusion implant typically includes at least one existing pedicle screw, at least one existing rod, and at least one existing connector interconnecting the existing pedicle screw to the existing rod. The extension implant comprises a rod, an offset beam connected to the rod, and a clamp interconnected to the offset beam, wherein the clamp can be secured to the existing rod, thereby extending the fusion construct. A method of use is also provided.

20 Claims, 4 Drawing Sheets

(56) References Cited

U.S. PATENT DOCUMENTS

| | | |
|---|---|---|
| 4,041,939 A | 8/1977 | Hall |
| 4,232,660 A | 11/1980 | Coles |
| 4,440,168 A | 4/1984 | Warren |
| 4,481,947 A | 11/1984 | Chester |
| 4,545,374 A | 10/1985 | Jacobson |
| 4,573,448 A | 3/1986 | Kambin |
| 4,617,922 A | 10/1986 | Griggs |
| 4,620,460 A | 11/1986 | Gonzales, Jr. |
| 4,686,972 A | 8/1987 | Kurland |
| 4,736,738 A | 4/1988 | Lipovsek et al. |
| 4,743,260 A | 5/1988 | Burton |
| 4,747,394 A | 5/1988 | Watanabe |
| 4,798,111 A | 1/1989 | Cheeseman |
| 4,803,976 A | 2/1989 | Frigg et al. |
| 4,817,587 A | 4/1989 | Janese |
| 4,862,891 A | 9/1989 | Smith |
| 4,863,423 A | 9/1989 | Wallace |
| 4,882,958 A | 11/1989 | McNeeley |
| 4,889,112 A | 12/1989 | Schachner et al. |
| 4,946,458 A | 8/1990 | Harms et al. |
| 4,995,875 A | 2/1991 | Coes |
| 5,002,542 A | 3/1991 | Frigg |
| 5,002,576 A | 3/1991 | Fuhrmann et al. |
| 5,018,507 A | 5/1991 | Montaldi |
| 5,024,213 A | 6/1991 | Asher et al. |
| 5,026,373 A | 6/1991 | Ray et al. |
| 5,030,220 A | 7/1991 | Howland |
| 5,030,223 A | 7/1991 | Anderson et al. |
| 5,035,232 A | 7/1991 | Lutze et al. |
| 5,048,379 A | 9/1991 | Gramera |
| 5,052,373 A | 10/1991 | Michelson |
| 5,055,104 A | 10/1991 | Ray |
| 5,084,043 A | 1/1992 | Hertzmann |
| 5,098,435 A | 3/1992 | Stednitz |
| 5,106,376 A | 4/1992 | Mononen |
| 5,129,899 A | 7/1992 | Small et al. |
| 5,129,900 A | 7/1992 | Asher et al. |
| 5,133,720 A | 7/1992 | Greenberg |
| 5,135,525 A | 8/1992 | Biscoping |
| 5,148,724 A | 9/1992 | Rexford |
| 5,158,543 A | 10/1992 | Lazarus |
| 5,165,306 A | 11/1992 | Hellon |
| 5,180,393 A | 1/1993 | Commarmond |
| 5,195,541 A | 3/1993 | Obenchain |
| 5,217,007 A | 6/1993 | Ciaglia |
| 5,275,600 A | 1/1994 | Allard et al. |
| 5,275,611 A | 1/1994 | Behl |
| 5,279,567 A | 1/1994 | Ciaglia |
| 5,282,863 A | 2/1994 | Burton |
| 5,292,309 A | 3/1994 | Van Tassel |
| 5,303,694 A | 4/1994 | Mikhail |
| 5,304,179 A | 4/1994 | Wagner |
| 5,306,275 A | 4/1994 | Bryan |
| 5,306,309 A | 4/1994 | Wagner et al. |
| 5,312,360 A | 5/1994 | Behl |
| 5,312,405 A | 5/1994 | Korotko et al. |
| 5,330,473 A | 7/1994 | Howland |
| 5,330,474 A | 7/1994 | Lin |
| 5,330,476 A | 7/1994 | Hiot et al. |
| 5,356,413 A | 10/1994 | Martins et al. |
| 5,363,841 A | 11/1994 | Coker |
| 5,387,213 A | 2/1995 | Breard et al. |
| 5,415,661 A | 5/1995 | Holmes |
| 5,423,816 A | 6/1995 | Lin |
| 5,431,639 A | 7/1995 | Shaw |
| 5,431,651 A | 7/1995 | Goble |
| D361,381 S | 8/1995 | Koros et al. |
| 5,439,464 A | 8/1995 | Shapiro |
| 5,466,238 A | 11/1995 | Lin |
| 5,472,426 A | 12/1995 | Bonati |
| 5,474,555 A | 12/1995 | Puno et al. |
| 5,480,401 A | 1/1996 | Navas |
| 5,484,440 A | 1/1996 | Allard |
| 5,489,274 A | 2/1996 | Chu |
| 5,489,308 A | 2/1996 | Kuslich et al. |
| 5,498,262 A | 3/1996 | Bryan |
| 5,499,983 A | 3/1996 | Hughes |
| 5,501,684 A | 3/1996 | Schlapfer et al. |
| 5,512,038 A | 4/1996 | O'Neal et al. |
| 5,545,166 A | 8/1996 | Howland |
| 5,549,612 A | 8/1996 | Yapp et al. |
| 5,558,622 A | 9/1996 | Greenberg |
| 5,562,663 A | 10/1996 | Wisnewski et al. |
| 5,565,502 A | 10/1996 | Glimcher et al. |
| 5,569,300 A | 10/1996 | Redmon |
| 5,584,831 A | 12/1996 | McKay |
| 5,584,833 A | 12/1996 | Fournet-Fayard et al. |
| 5,591,166 A | 1/1997 | Bernhardt et al. |
| 5,591,235 A | 1/1997 | Kuslich |
| 5,593,409 A | 1/1997 | Michelson |
| 5,601,550 A | 2/1997 | Esser |
| 5,603,714 A | 2/1997 | Kaneda et al. |
| 5,611,778 A | 3/1997 | Brinon |
| 5,613,968 A | 3/1997 | Lin |
| 5,628,740 A | 5/1997 | Mullane |
| 5,630,816 A | 5/1997 | Kambin |
| 5,643,263 A | 7/1997 | Simonson |
| 5,643,264 A | 7/1997 | Sherman et al. |
| 5,645,544 A | 7/1997 | Tai et al. |
| 5,645,599 A | 7/1997 | Samani |
| 5,649,925 A | 7/1997 | Barbera Alacreu |
| 5,667,506 A | 9/1997 | Sutterlin |
| 5,672,175 A | 9/1997 | Martin |
| 5,683,389 A | 11/1997 | Orsak |
| 5,683,392 A | 11/1997 | Richelsoph et al. |
| 5,683,463 A | 11/1997 | Godefroy et al. |
| 5,687,739 A | 11/1997 | McPherson |
| 5,690,632 A | 11/1997 | Schwartz et al. |
| 5,691,397 A | 11/1997 | Glimcher et al. |
| 5,695,993 A | 12/1997 | Fukudome et al. |
| 5,702,455 A | 12/1997 | Saggar |
| 5,716,355 A | 2/1998 | Jackson et al. |
| 5,716,415 A | 2/1998 | Steffee |
| 5,725,528 A | 3/1998 | Errico et al. |
| 5,735,850 A | 4/1998 | Baumgartner et al. |
| 5,735,851 A | 4/1998 | Errico et al. |
| 5,735,899 A | 4/1998 | Schwartz et al. |
| 5,743,853 A | 4/1998 | Lauderdale |
| 5,746,720 A | 5/1998 | Stouder, Jr. |
| 5,746,741 A | 5/1998 | Kraus et al. |
| 5,752,957 A | 5/1998 | Ralph et al. |
| 5,766,221 A | 6/1998 | Benderev et al. |
| 5,766,253 A | 6/1998 | Brosnahan, III |
| 5,772,582 A | 6/1998 | Huttner et al. |
| 5,782,832 A | 7/1998 | Larsen et al. |
| 5,785,648 A | 7/1998 | Min |
| 5,785,710 A | 7/1998 | Michelson |
| 5,785,712 A | 7/1998 | Runciman et al. |
| 5,792,044 A | 8/1998 | Foley |
| 5,797,912 A | 8/1998 | Runciman et al. |
| 5,800,435 A | 9/1998 | Errico et al. |
| 5,810,816 A | 9/1998 | Roussouly et al. |
| 5,810,817 A | 9/1998 | Roussouly et al. |
| D399,955 S | 10/1998 | Koros et al. |
| 5,819,257 A | 10/1998 | Monge et al. |
| 5,827,328 A | 10/1998 | Buttermann |
| 5,836,948 A | 11/1998 | Zucherman et al. |
| RE36,020 E | 12/1998 | Moore et al. |
| 5,851,207 A | 12/1998 | Cesarone |
| 5,860,977 A | 1/1999 | Zucherman et al. |
| 5,865,847 A | 2/1999 | Kohrs et al. |
| 5,865,848 A | 2/1999 | Baker |
| 5,876,404 A | 3/1999 | Zucherman et al. |
| 5,882,344 A | 3/1999 | Stouder, Jr. |
| 5,885,285 A | 3/1999 | Simonson |
| 5,885,299 A | 3/1999 | Winslow et al. |
| 5,885,300 A | 3/1999 | Tokuhashi et al. |
| 5,891,147 A | 4/1999 | Moskovitz et al. |
| 5,895,352 A | 4/1999 | Kleiner |
| 5,895,390 A | 4/1999 | Moran et al. |
| 5,897,593 A | 4/1999 | Kohrs et al. |
| 5,899,901 A | 5/1999 | Middleton |
| 5,902,231 A | 5/1999 | Foley |
| 5,902,304 A | 5/1999 | Walker et al. |

(56) References Cited

U.S. PATENT DOCUMENTS

| | | |
|---|---|---|
| 5,904,650 A | 5/1999 | Wells |
| 5,906,616 A | 5/1999 | Pavlov et al. |
| 5,913,818 A | 6/1999 | Co et al. |
| 5,928,139 A | 7/1999 | Koros |
| 5,928,233 A | 7/1999 | Apfelbaum et al. |
| 5,931,838 A | 8/1999 | Vito |
| 5,938,663 A | 8/1999 | Petreto |
| 5,944,658 A | 8/1999 | Koros et al. |
| 5,947,965 A | 9/1999 | Bryan |
| 5,954,635 A | 9/1999 | Foley |
| 5,954,671 A | 9/1999 | O'Neill |
| 5,961,516 A | 10/1999 | Graf |
| 5,967,970 A | 10/1999 | Cowan |
| 5,968,098 A | 10/1999 | Winslow |
| 5,971,920 A | 10/1999 | Nagel |
| 5,976,135 A | 11/1999 | Sherman et al. |
| 5,976,146 A | 11/1999 | Ogawa |
| 5,984,924 A | 11/1999 | Asher et al. |
| 5,996,447 A | 12/1999 | Bayouth |
| 5,997,539 A | 12/1999 | Errico et al. |
| 6,004,322 A | 12/1999 | Bernstein |
| 6,007,487 A | 12/1999 | Foley et al. |
| 6,010,520 A | 1/2000 | Pattison |
| 6,017,342 A | 1/2000 | Rinner |
| 6,027,533 A | 2/2000 | Olerud |
| 6,045,579 A | 4/2000 | Hochshuler et al. |
| 6,048,342 A | 4/2000 | Zucherman et al. |
| 6,050,997 A | 4/2000 | Mullane |
| 6,063,088 A | 5/2000 | Winslow |
| 6,068,630 A | 5/2000 | Zucherman et al. |
| 6,074,390 A | 6/2000 | Zucherman et al. |
| 6,074,393 A | 6/2000 | Sitoto |
| 6,080,155 A | 6/2000 | Michelson |
| 6,080,193 A | 6/2000 | Hochshuler et al. |
| 6,081,741 A | 6/2000 | Hollis |
| 6,083,225 A | 7/2000 | Winslow et al. |
| 6,083,226 A | 7/2000 | Fiz |
| 6,090,112 A | 7/2000 | Zucherman et al. |
| 6,102,948 A | 8/2000 | Brosnahan, III |
| 6,113,602 A | 9/2000 | Sand |
| 6,117,137 A | 9/2000 | Halm et al. |
| 6,117,174 A | 9/2000 | Nolan |
| 6,120,434 A | 9/2000 | Kimura |
| 6,120,506 A | 9/2000 | Kohrs et al. |
| 6,123,705 A | 9/2000 | Michelson |
| 6,123,706 A | 9/2000 | Lange |
| 6,132,430 A | 10/2000 | Wagner |
| D433,296 S | 11/2000 | Yamakawa |
| 6,146,383 A | 11/2000 | Studer et al. |
| 6,149,652 A | 11/2000 | Zucherman et al. |
| 6,149,686 A | 11/2000 | Kuslish et al. |
| 6,152,871 A | 11/2000 | Foley |
| 6,152,926 A | 11/2000 | Zucherman et al. |
| 6,156,006 A | 12/2000 | Brosens |
| 6,156,038 A | 12/2000 | Zucherman et al. |
| 6,159,179 A | 12/2000 | Simonson |
| 6,162,170 A | 12/2000 | Foley |
| 6,162,236 A | 12/2000 | Osada |
| D436,513 S | 1/2001 | Yamakawa |
| 6,176,823 B1 | 1/2001 | Foley |
| 6,176,861 B1 | 1/2001 | Bernstein et al. |
| 6,179,838 B1 | 1/2001 | Fiz |
| D438,074 S | 2/2001 | Marr |
| 6,183,471 B1 | 2/2001 | Zucherman et al. |
| 6,187,005 B1 | 2/2001 | Brace et al. |
| 6,190,387 B1 | 2/2001 | Zucherman et al. |
| 6,190,414 B1 | 2/2001 | Young et al. |
| 6,196,696 B1 | 3/2001 | Shiao |
| 6,196,969 B1 | 3/2001 | Bester et al. |
| 6,197,002 B1 | 3/2001 | Peterson |
| 6,206,822 B1 | 3/2001 | Foley |
| 6,206,826 B1 | 3/2001 | Mathews et al. |
| 6,206,885 B1 | 3/2001 | Ghahremani et al. |
| 6,206,922 B1 | 3/2001 | Zdeblick et al. |
| 6,206,923 B1 | 3/2001 | Boyd et al. |
| 6,210,413 B1 | 4/2001 | Justis et al. |
| 6,217,509 B1 | 4/2001 | Foley |
| 6,224,597 B1 | 5/2001 | Coker |
| 6,224,608 B1 | 5/2001 | Ciccolella |
| 6,224,631 B1 | 5/2001 | Kohrs |
| 6,231,575 B1 | 5/2001 | Krag |
| 6,235,030 B1 | 5/2001 | Zucherman et al. |
| 6,238,397 B1 | 5/2001 | Zucherman et al. |
| 6,245,072 B1 | 6/2001 | Zdeblick et al. |
| 6,248,104 B1 | 6/2001 | Chopin et al. |
| 6,248,106 B1 | 6/2001 | Ferree |
| 6,258,097 B1 | 7/2001 | Cook |
| 6,261,287 B1 | 7/2001 | Metz-Stavenhagen |
| 6,264,658 B1 | 7/2001 | Lee et al. |
| 6,267,763 B1 | 7/2001 | Castro |
| 6,267,764 B1 | 7/2001 | Elberg |
| 6,267,765 B1 | 7/2001 | Taylor et al. |
| 6,270,498 B1 | 8/2001 | Michelson |
| 6,273,914 B1 | 8/2001 | Papas |
| 6,273,917 B1 | 8/2001 | Inoue |
| 6,283,966 B1 | 9/2001 | Houfburg |
| 6,287,309 B1 | 9/2001 | Baccelli et al. |
| 6,287,313 B1 | 9/2001 | Sasso |
| 6,287,343 B1 | 9/2001 | Kuslich et al. |
| 6,290,700 B1 | 9/2001 | Schmotzer |
| 6,293,949 B1 | 9/2001 | Justis et al. |
| 6,296,609 B1 | 10/2001 | Brau |
| 6,299,614 B1 | 10/2001 | Kretschmer et al. |
| 6,302,842 B1 | 10/2001 | Auerbach et al. |
| 6,309,390 B1 | 10/2001 | Le Couedic et al. |
| 6,309,391 B1 | 10/2001 | Crandall et al. |
| 6,312,432 B1 | 11/2001 | Leppelmeier |
| 6,332,883 B1 | 12/2001 | Zucherman et al. |
| 6,342,057 B1 | 1/2002 | Brace |
| 6,348,058 B1 | 2/2002 | Melkent et al. |
| 6,354,176 B1 | 3/2002 | Nordlin |
| 6,355,038 B1 | 3/2002 | Pisharodi |
| 6,361,541 B1 | 3/2002 | Barnhart |
| D455,766 S | 4/2002 | Marty |
| 6,368,320 B1 | 4/2002 | Le Couedic et al. |
| 6,368,350 B1 | 4/2002 | Erickson et al. |
| 6,368,351 B1 | 4/2002 | Glenn et al. |
| 6,371,959 B1 | 4/2002 | Trice |
| 6,371,968 B1 | 4/2002 | Kogasaka et al. |
| 6,379,354 B1 | 4/2002 | Rogozinski |
| 6,391,058 B1 | 5/2002 | Kuslich et al. |
| 6,395,033 B1 | 5/2002 | Pepper |
| 6,418,821 B1 | 7/2002 | Yamakawa |
| 6,425,901 B1 | 7/2002 | Zhu et al. |
| 6,428,472 B1 | 8/2002 | Haas |
| 6,440,169 B1 | 8/2002 | Elberg et al. |
| 6,440,170 B1 | 8/2002 | Jackson |
| 6,443,953 B1 | 9/2002 | Perra et al. |
| 6,443,989 B1 | 9/2002 | Jackson |
| 6,461,330 B1 | 10/2002 | Miyagi |
| 6,461,359 B1 | 10/2002 | Tribus et al. |
| 6,471,724 B2 | 10/2002 | Zdeblick et al. |
| 6,475,219 B1 | 11/2002 | Shelokov |
| 6,478,798 B1 | 11/2002 | Howland |
| 6,506,151 B2 | 1/2003 | Estes et al. |
| 6,520,907 B1 | 2/2003 | Foley |
| 6,524,238 B2 | 2/2003 | Velikaris et al. |
| 6,530,880 B2 | 3/2003 | Pagliuca |
| 6,530,926 B1 | 3/2003 | Davidson |
| 6,540,756 B1 | 4/2003 | Vaughan |
| 6,551,320 B2 | 4/2003 | Lieberman |
| 6,554,831 B1 | 4/2003 | Rivard et al. |
| 6,562,046 B2 | 5/2003 | Sasso |
| 6,562,073 B2 | 5/2003 | Foley |
| 6,565,569 B1 | 5/2003 | Assaker et al. |
| 6,569,164 B1 | 5/2003 | Assaker et al. |
| 6,576,017 B2 | 6/2003 | Foley et al. |
| 6,579,292 B2 | 6/2003 | Taylor |
| 6,585,738 B1 | 7/2003 | Mangione et al. |
| 6,585,769 B1 | 7/2003 | Muhanna et al. |
| 6,595,993 B2 | 7/2003 | Donno et al. |
| 6,610,062 B2 | 8/2003 | Bailey et al. |
| 6,626,904 B1 | 9/2003 | Jammet et al. |
| 6,626,906 B1 | 9/2003 | Young |

(56) References Cited

U.S. PATENT DOCUMENTS

| | | |
|---|---|---|
| 6,648,887 B2 | 11/2003 | Ashman |
| 6,652,527 B2 | 11/2003 | Zucherman et al. |
| 6,671,725 B1 | 12/2003 | Noel, Jr. et al. |
| 6,676,661 B1 | 1/2004 | Benlloch et al. |
| 6,679,833 B2 | 1/2004 | Smith et al. |
| 6,682,532 B2 | 1/2004 | Johnson et al. |
| 6,685,705 B1 | 2/2004 | Taylor |
| 6,692,434 B2 | 2/2004 | Ritland |
| 6,736,816 B2 | 5/2004 | Ritland |
| 6,743,257 B2 | 6/2004 | Castro |
| 6,749,613 B1 | 6/2004 | Conchy et al. |
| 6,749,614 B2 | 6/2004 | Teitelbaum et al. |
| 6,752,832 B2 | 6/2004 | Neumann |
| 6,761,719 B2 | 7/2004 | Justis et al. |
| 6,783,528 B2 | 8/2004 | Vincent-Prestigiacomo |
| 6,851,430 B2 | 2/2005 | Tsou |
| 6,875,211 B2 | 4/2005 | Nichols et al. |
| 6,916,319 B2 | 7/2005 | Munting |
| 6,916,330 B2 | 7/2005 | Simonson |
| 6,929,606 B2 | 8/2005 | Ritland |
| 6,951,538 B2 | 10/2005 | Ritland |
| 6,955,678 B2 | 10/2005 | Gabriel et al. |
| 6,966,910 B2 | 11/2005 | Ritland |
| 6,974,480 B2 | 12/2005 | Messerli et al. |
| 6,991,632 B2 | 1/2006 | Ritland |
| 7,008,421 B2 | 3/2006 | Daniel et al. |
| 7,115,142 B2 | 10/2006 | Muhanna et al. |
| 7,166,073 B2 | 1/2007 | Ritland |
| 7,207,992 B2 | 4/2007 | Ritland |
| 7,344,539 B2 | 3/2008 | Serhan et al. |
| 7,758,582 B2 * | 7/2010 | Ferrante et al. ............... 606/96 |
| 7,766,943 B1 | 8/2010 | Fallin et al. |
| 2001/0005796 A1 | 6/2001 | Zdeblick et al. |
| 2001/0010021 A1 | 7/2001 | Boyd et al. |
| 2001/0012942 A1 | 8/2001 | Estes |
| 2001/0027320 A1 | 10/2001 | Sasso |
| 2001/0047207 A1 | 11/2001 | Michelson |
| 2002/0011135 A1 | 1/2002 | Hall |
| 2002/0013586 A1 | 1/2002 | Justis |
| 2002/0016592 A1 | 2/2002 | Branch |
| 2002/0022764 A1 | 2/2002 | Smith |
| 2002/0029082 A1 | 3/2002 | Muhanna |
| 2002/0049368 A1 | 4/2002 | Ritland |
| 2002/0052603 A1 | 5/2002 | Nichols et al. |
| 2002/0058948 A1 | 5/2002 | Arlettaz |
| 2002/0068973 A1 | 6/2002 | Jackson |
| 2002/0068975 A1 | 6/2002 | Teitelbaum et al. |
| 2002/0077632 A1 | 6/2002 | Tsou |
| 2002/0082695 A1 | 6/2002 | Neumann |
| 2002/0107571 A1 | 8/2002 | Foley |
| 2002/0107572 A1 | 8/2002 | Foley et al. |
| 2002/0111625 A1 | 8/2002 | Richelsoph et al. |
| 2002/0120270 A1 | 8/2002 | Trieu et al. |
| 2002/0123668 A1 | 9/2002 | Ritland |
| 2002/0143235 A1 | 10/2002 | Pagliuca |
| 2003/0045874 A1 | 3/2003 | Thomas |
| 2003/0083688 A1 | 5/2003 | Simonson |
| 2003/0083689 A1 | 5/2003 | Simonson |
| 2003/0093078 A1 | 5/2003 | Ritland |
| 2003/0109880 A1 | 6/2003 | Shirado et al. |
| 2003/0139812 A1 | 7/2003 | Garcia et al. |
| 2003/0144665 A1 | 7/2003 | Munting |
| 2003/0171749 A1 | 9/2003 | Le Couedic et al. |
| 2003/0171751 A1 | 9/2003 | Ritland |
| 2003/0187431 A1 | 10/2003 | Simonson |
| 2003/0220689 A1 | 11/2003 | Ritland |
| 2003/0236447 A1 | 12/2003 | Ritland |
| 2004/0002708 A1 | 1/2004 | Ritland |
| 2004/0073215 A1 | 4/2004 | Carli |
| 2004/0106997 A1 | 6/2004 | Lieberson |
| 2004/0138534 A1 | 7/2004 | Ritland |
| 2004/0172023 A1 | 9/2004 | Ritland |
| 2004/0181223 A1 | 9/2004 | Ritland |
| 2004/0254428 A1 | 12/2004 | Ritland |
| 2005/0004593 A1 | 1/2005 | Simonson |
| 2005/0020920 A1 | 1/2005 | Ritland |
| 2005/0027360 A1 | 2/2005 | Webb et al. |
| 2005/0119656 A1 | 6/2005 | Ferrante et al. |
| 2005/0143737 A1 | 6/2005 | Paffard et al. |
| 2005/0149023 A1 | 7/2005 | Ritland |
| 2005/0149191 A1 | 7/2005 | Cragg et al. |
| 2005/0203517 A1 | 9/2005 | Jahng et al. |
| 2005/0203519 A1 | 9/2005 | Harms et al. |
| 2005/0209694 A1 | 9/2005 | Loeb |
| 2005/0228233 A1 | 10/2005 | Ritland |
| 2006/0009768 A1 | 1/2006 | Ritland |
| 2006/0025770 A1 | 2/2006 | Schlapfer et al. |
| 2006/0041259 A1 | 2/2006 | Paul et al. |
| 2006/0064090 A1 | 3/2006 | Park |
| 2006/0069390 A1 | 3/2006 | Frigg et al. |
| 2006/0079899 A1 | 4/2006 | Ritland |
| 2006/0085076 A1 * | 4/2006 | Krishna et al. ............. 623/17.15 |
| 2006/0195087 A1 * | 8/2006 | Sacher et al. ................ 606/61 |
| 2006/0265074 A1 | 11/2006 | Krishna et al. |
| 2006/0276794 A1 * | 12/2006 | Stern ............................ 606/69 |
| 2007/0016193 A1 | 1/2007 | Ritland |
| 2007/0233090 A1 | 10/2007 | Naifeh et al. |
| 2008/0071275 A1 | 3/2008 | Ferree |

FOREIGN PATENT DOCUMENTS

| | | |
|---|---|---|
| EP | 0820731 | 1/1998 |
| EP | 1585427 | 11/2003 |
| EP | 1658815 | 5/2006 |
| FR | 2735351 | 12/1996 |
| FR | 2755844 | 5/1998 |
| FR | 2767669 | 3/1999 |
| FR | 2796828 | 2/2001 |
| FR | 2799949 | 4/2001 |
| FR | 2812185 | 2/2002 |
| JP | 6-3551 | 2/1994 |
| JP | 6-165788 | 6/1994 |
| JP | H07-008504 | 1/1995 |
| JP | H11-501235 | 2/1999 |
| JP | H11-502742 | 3/1999 |
| JP | 2000-33091 | 2/2000 |
| WO | 95/08298 | 3/1995 |
| WO | 96/29947 | 10/1996 |
| WO | 97/06742 | 2/1997 |
| WO | 97/32533 | 9/1997 |
| WO | 99/40866 | 8/1999 |
| WO | 00/18306 | 4/2000 |
| WO | 00/57801 | 10/2000 |
| WO | 01/64144 | 9/2001 |
| WO | 01/67973 | 9/2001 |
| WO | 02/07621 | 1/2002 |
| WO | 02/36026 | 1/2002 |
| WO | 02/060330 | 8/2002 |
| WO | 02/002022 | 10/2002 |
| WO | 02/102259 | 12/2002 |
| WO | 03/026523 | 4/2003 |
| WO | 03/073908 | 9/2003 |
| WO | 03/094699 | 11/2003 |
| WO | 03/105704 | 12/2003 |
| WO | 2004/052218 | 6/2004 |
| WO | 2004/075778 | 9/2004 |
| WO | 2004/089244 | 10/2004 |

OTHER PUBLICATIONS

International Search Report dated Sep. 10, 2007, issued in Application No. PCT/US06/28100.

Written Opinion dated Sep. 10, 2007, issued in Application No. PCT/US06/28100.

International Preliminary Report on Patentability dated Jan. 22, 2008, issued in Application No. PCT/US06/28100.

Office Action dated Feb. 5, 2009, issued in U.S. Appl. No. 11/458,629.

Final Office Action dated Oct. 8, 2009, issued in U.S. Appl. No. 11/458,629.

Office Action dated Dec. 23, 2010, issued in U.S. Appl. No. 11/458,629.

(56) References Cited

OTHER PUBLICATIONS

Examiner Interview Summary dated Apr. 22, 2011, issued in U.S. Appl. No. 11/458,629.
Notice of Allowance dated Jul. 28, 2011, issued in U.S. Appl. No. 11/458,629.
Office Action dated Aug. 20, 2011, issued in Australian Application No. 200629900.
Extended Search Report dated Nov. 3, 2010, issued in European Application No. 06787906.4.
Office Action dated Nov. 22, 2010, issued in European Application No. 06787906.4.
Office Action dated Jun. 24, 2011 issued in European Application No. 06787906.4.
Office Action dated Feb. 24, 2012, issued in European Application No. 06787906.4.
Office Action dated Jan. 11, 2011, issued in Japanese Application No. 2008-522944.
Office Action dated Sep. 13, 2011, issued in Japanese Application No. 2008-522944.
CASPAR "Technique of Microsurgery: Microsurgery of the Lumbar Spine: Principles and Techniques in Spine Surgery"; Aspen Publications; 1990; 105-122.
China Chemical Reporter, "Rapid Development of Polyether Ether Ketone", CNCIC Chemdata Inc 2004, 2 pages.
Green, "Body Building—Medical Materials for Systems and Scaffolding," Materials World, Journal of the Institute of Materials, vol. 10, No. 2, 2001, 4 pages.
Green, "Effects of Gamma Sterilisation on Implant Grade Polyetheretherketone," Invibio Inc, Lancashire, United Kingdom, undated, 1 page.
Green, "In Vivo Biostability Study on Polyaryletheretherketone Biomaterial," Invibio Inc Lancashire, United Kingdom, undated, 2 pages.
Green, et al. "A Polyaryletherketone Biomaterial for Use in Medical Implant Applications," Lancashire, United Kingdom, 2001, 1 page.
Green, et al. "Polyetheretherketone Polymer and Compounds for Surgical Applications," Lancashire, United Kingdom, undated, 9 pages.
Green, Stuart, "Peek-Optima Polymer in the Implantable Medical Device Industry," Invibio Inc Lancashire, United Kingdom, undated, 2 pages.
Hilton et al.; "Meditronic Sofamor Danek METRX Microdiscectomy Surgical Technique Brochure"; 2000.
Invibio, Biomaterials Solutions, "High Performance PEEK-Optima Biocompatible Polymer Chosen for Dental Abutment Healing Caps," Invibio Inc Lancashire, United Kingdom, undated, 1 page.
Invibio, Biomaterials Solutions, "High Performance PEEK-Optima Biocompatible Polymer Chosen for New Generation Heart Valve," Invibio Inc., Lancashire, United Kingdom, undated, 1 page.
Invibio, Biomaterials Solutions, "PEEK~Classix," Invibio Inc., Lancashire, United Kingdom, 2003, 2 pages.
Invibio, Biomaterials Solutions, "Peek-Optima Polymer: Performance Purity Flexibility Endurance," Invibio Inc., Lancashire, United Kingdom, 2004, 3 pages.
Invibio, Biomaterials Solutions, "PEEK-Optima, Composite Hip," Invibio Inc., Lancashire, United Kingdom, undated, 2 pages.
Invibio, Biomaterials Solutions, "Peek-Optima, Spiked Washers," Invibio Inc., Lancashire, United Kingdom, undated, 1 page.
Kambin; "Arthroscopic Microdiscectomy: Minimal Intervention in Spinal Surgery"; National Ubrary of Medicine; 1991; 67-100.
Kambin; "Percutaneous Posterolateral Discectomy"; Clincial Orthopaedics and Related Research. Section II; 145-154119.
Savitz; "Same-Day Microsurgical Arthroscopic Latera-Approach Laser-Assisted (SMALL) Fluoroscopic Discectomy"; Journal of Neurosurgery; Jun. 1994; 1039-1045.
Schaffer et al.; "Percutaneous Posterolateral Lumbar Discectomy and Decompression with a 6.9 Millimeter Cannula"; Journal of Bone and Joint Surgery; 1991; 822-831.
Sofamor Danek Video Systems Brochure.
"New Minimally Invasive Techniques, Improve Outcome of Spine Surgeries", Medtronic Sofamor Danek.
Tangram Technology Ltd., "Polymer Data File: Polyether Ether Keotone—PEEK," Available at http://www.tangram.co.uk/TI-Polymer-PEEK.html, 2001, 5 pages.
Web pages, http://brainlab.com, Apr. 2, 2002; 5 pages.
Wiltse; "New Uses and Refinements of the Paraspinal Approach to the Lumbar Spine"; Spine; 1988; 13(6):696-706.

* cited by examiner

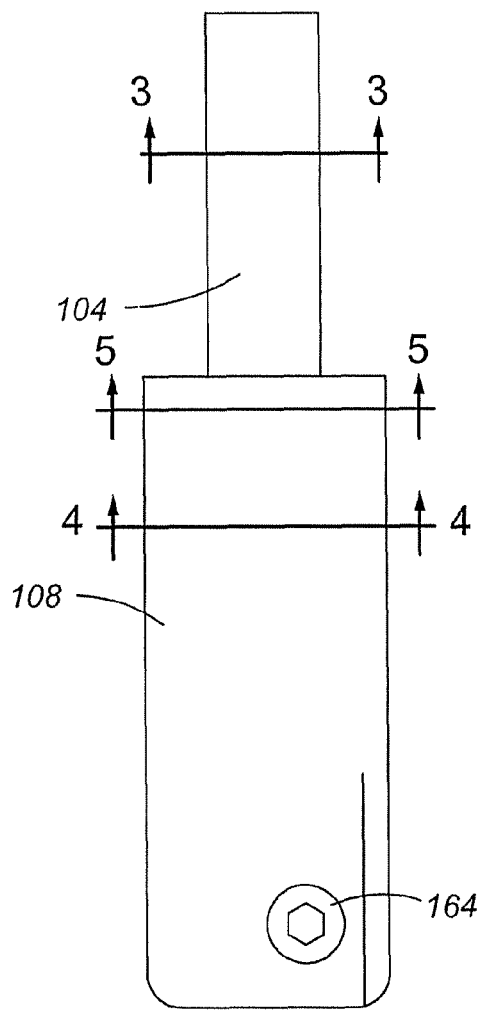
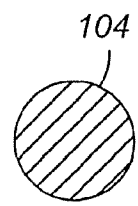
Fig. 3
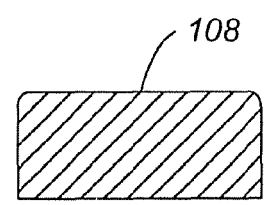
Fig. 4
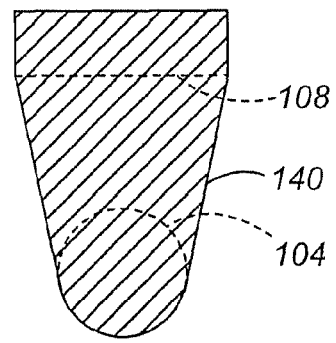
Fig. 2  Fig. 5

ROD EXTENSION FOR EXTENDING FUSION CONSTRUCT

CROSS REFERENCE TO RELATED APPLICATIONS

The present application is a divisional application of U.S. patent application Ser. No. 11/458,629 filed Jul. 19, 2006, which claims the benefit of U.S. Provisional Patent Application No. 60/700,887 filed on Jul. 19, 2005, both of which are incorporated herein by reference in their entireties.

FIELD OF THE INVENTION

The present invention pertains to spinal implants, and more specifically, to a device for extending a pre-existing implant having a rod component.

BACKGROUND OF THE INVENTION

At times, spinal surgeons are faced with the problem of having to add additional length to a fusion rod that spans one or more intervertebral disks. For example, a patient may have had a previous surgery whereby they received an implant spanning a single lumbar disk, wherein the implant serves to structurally fuse the vertebra on either side of the disk using pedicle screws that are connected to a rigid rod that bridges the disk.

If the patient then develops a problem with an adjacent disk, the surgeon is faced with having to somehow bridge the adjacent disk; however, a location to anchor the first end of the new fusion implant is already taken up by the existing implant. Accordingly, surgeons typically open the region of the existing implant and install a new implant that spans the length of the first implant, as well as the additional disk that has become problematic. This existing solution causes the disruption of the area of the first implant, and therefore, results in additional tissue damage and required healing time, added surgical time, and added corresponding treatment costs.

Accordingly, it would be advantageous to be able to attach the new implant to the existing implant without removing the first implant or unnecessarily disrupting or causing tissue damage to the area of the existing implant.

SUMMARY OF THE INVENTION

In accordance with embodiments of the present invention, a spinal fusion extension implant is provided for interconnecting to an existing fusion implant in a spine of a patient, the existing fusion implant having at least one existing pedicle screw, at least one existing rod, and at least one existing connector interconnecting the existing pedicle screw to the existing rod, the extension implant comprising a rod, an offset beam connected to the rod; and a clamp connected to the offset beam, wherein the clamp is adapted to be secured to the existing rod.

In accordance with embodiments of the present invention, an extension implant is provided, wherein the clamp comprises a receptacle for receiving at least a portion of the existing rod and the receptacle comprises opposing arms that extend around at least an equator of the existing rod.

In accordance with embodiments of the present invention, an extension implant is provided, wherein the clamp comprises a deformable body having a slot with first and second sides, the deformable body having a first wing on the first slot side and a second wing on the second slot side.

In accordance with embodiments of the present invention an extension implant is provided, further comprising a screw for deforming at least one of the first or second wings away from the other of the first or second wings.

In accordance with embodiments of the present invention, an extension implant is provided, wherein the rod portion and the offset beam are connected by means of a transitional section.

In accordance with embodiments of the present invention a spinal fusion extension implant is provided for interconnecting to an existing fusion implant in a spine of a patient, the existing fusion implant having at least one existing pedicle screw, at least one existing rod, and at least one existing connector interconnecting the existing pedicle screw to the existing rod, the extension implant comprising a means for longitudinally stabilizing at least a portion of the spine, a means for offsetting around at least one of the existing pedicle screw and the existing connector, the means for offsetting connected to the means for longitudinally stabilizing, and a means for clamping connected to the means for offsetting, wherein the means for clamping secures the means for longitudinally stabilizing and the means for offsetting to the existing rod.

In accordance with embodiments of the present invention, a clamp is provided for attaching a first spinal implant member to a second spinal implant member, comprising a deformable body, a receptacle, within the deformable body, for receiving at least a portion of the second spinal implant member, the receptacle comprising opposing arms, wherein the opposing arms extend around at least an equator of the second spinal implant member, a slot, within the deformable body, wherein the slot separates a first and second wing of the deformable body; and a screw for tightening the clamp, wherein the screw operates to separate the first and second wings and wherein the separation results in a deformation of the deformable body, whereby the deformation results in a closing of the receptacle around the at least a portion of the second spinal implant member.

In accordance with embodiments of the present invention, a clamp is provided further comprising a screw hole, within the deformable body, extending through the first wing of the deformable body, the screw hole adapted to receive the screw to facilitate contact with the second wing of the deformable body.

In accordance with embodiments of the present invention, a method for extending a spinal rod is provided, comprising the steps of installing a pedicle screw into a vertebra adjacent an existing spinal implant, connecting the pedicle screw to a portion of a spinal rod extension, having a clamp operatively associated therewith, the clamp having at least one receptacle adapted to receive a rod and being deformable to secure the rod, inserting into the receptacle a rod portion of the existing implant, and deforming the clamp to secure the rod portion of the existing spinal implant.

BRIEF DESCRIPTION OF THE DRAWINGS

FIG. 2 is a top plan view of the embodiment of the present invention shown in FIG. 1a;

FIG. 3 is a cross-sectional view of a rod portion of the embodiment of the present invention shown in FIG. 2;

FIG. 4 is a cross-sectional view of an offset beam portion of the embodiment of the present invention shown in FIG. 2;

FIG. 5 is a cross-sectional view of a transitional rod-to-offset beam portion of the embodiment of the present invention shown in FIG. 2.

Drawings are not necessarily to scale.

DETAILED DESCRIPTION

In accordance with embodiments of the present invention, a rod extension for extending a fusion construct is provided. The rod extension allows a surgeon to connect a stabilization rod implant to at least a portion of a patient's spine, and also connect the stabilization rod implant to an existing implant that has been previously installed in the patient. In various embodiments of the present invention a device is provided that may be used to extend an existing fusion rod implant cephalad and caudal.

Figure 1A:
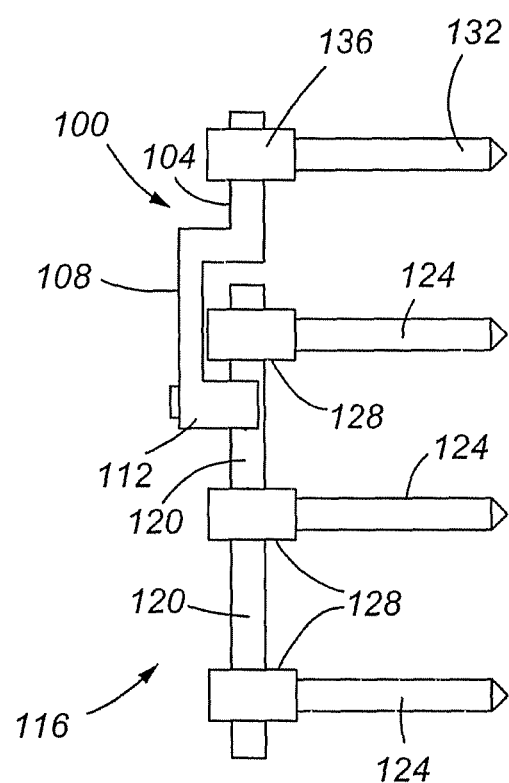
FIG. 1a is a side elevation view of an existing implant and of an embodiment of the present invention connected to the implant.

Referring now to FIG. 1a, rod extension 100 is shown in accordance with embodiments of the present invention. The rod extension 100 provides for a simple, rigid connection to an existing fusion rod. The rod extension 100 generally includes a rod portion 104, an offset beam 108, and a clamp 112. As shown in FIG. 1a, the rod extension 100 is connected to an existing fusion implant 116, wherein the existing fusion implant 116 comprises an existing rod 120, existing pedicle screws 124, and existing connectors 128 that interconnect the existing rod 120 to the existing pedicle screws 124.

Referring still to FIG. 1a, in accordance with embodiments of the present invention, the rod extension 100 is of sufficient length to allow the device to be anchored to the spine at the end comprising the rod portion 104, while at the other end extending sufficient distance to be connected to an existing implant 116. The end comprising the rod portion 104 may be anchored to the spine using hooks or other means to be attached to the spine. As shown in FIG. 1a, a pedicle screw 132 is shown interconnected to the rod 104 using a connector 136, wherein the pedicle screw 132 may be inserted into the pedicle of a vertebra for anchoring the end comprising the rod portion 104 to the spine. In accordance with embodiments of the present invention, the offset beam 108 comprises a means for stepping over or around the screw head of an existing pedicle screw 124 and existing connector 128, thereby allowing the rod portion 104 of the rod extension 100 to be substantially aligned with the existing rod 120. The offset beam 108, therefore, is of sufficient dimensions to allow the rod extension 100 to have access to the existing rod 120 via clamp 112, while also providing clearance from the screw head of an existing screw 124 and its associated existing connector 128. In accordance with embodiments of the present invention, the offset beam 108 may further comprise a telescoping means or other means for adjusting its longitudinal length and/or its offset or step dimension to accommodate different implant systems and/or to further accommodate actual conditions found within each patient.

FIG. 1a illustrates one possible orientation of existing rod 120, rod portion 104, offset beam 108, and clamp 112. In particular, existing rod 120 and offset beam 108 are shown to be parallel. Additionally, existing rod 120 and rod portion 104 are shown to be collinear. It should be understood, however, that other orientations are within the scope of the invention. For example, existing rod 120 and offset beam 108 may be oriented at an angle or existing rod 120 and rod portion 104 may not be collinear. Differing orientations may be needed to accommodate the unique dimensions of the various spinal structures of individual patients. In addition, the various elements of the rod extension may be oriented to accommodate the natural curvature of the spine. Furthermore, all of the drawings contained herein are for illustration purposes and should not be considered to scale.

Figure 1B:
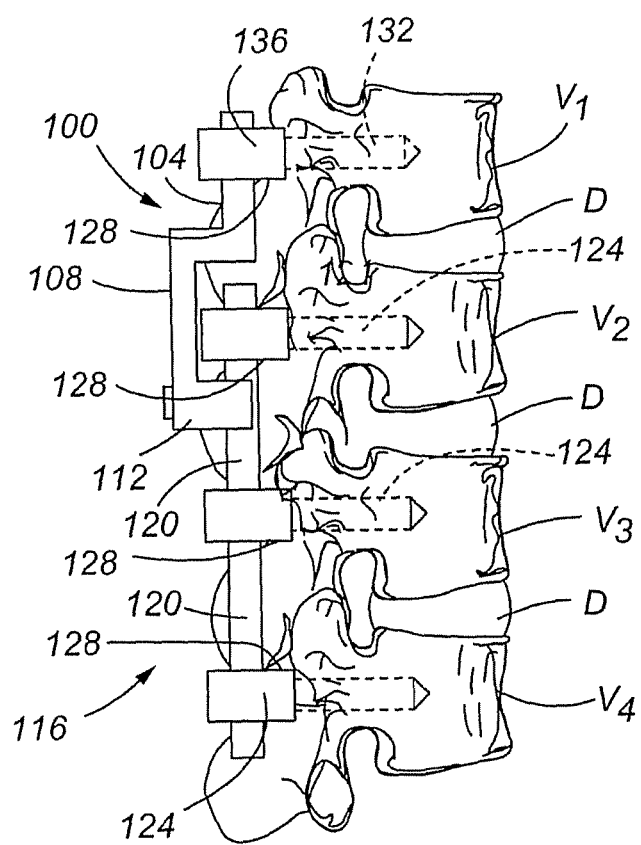
FIG. 1b is a side elevation view of the existing implant and embodiment of the present invention shown in FIG. 1b, shown here attached to a spine.

Referring now to FIG. 1b, a rod extension 100, in accordance with embodiments of the present invention, is shown attached to a human spine. FIG. 1b shows vertebrae V1, V2, V3, and V4 separated by disks D. The existing spinal fusion implant 116 is shown anchored to vertebrae V2, V3, and V4. The spinal extension 100 is shown anchored to vertebra V1 and attached to the existing spinal fusion implant 116 by means of connector 112.

Referring to FIG. 2, a top plan view of the rod extension 100 is shown. The rod extension 100 is shown with a rod portion 104 at a first end of the extension 100, and the offset beam 108 with the clamp portion 112 at the other end of the rod extension 100. FIG. 3 shows a cross-sectional view of the rod portion 104. The rod portion 104 is shown to have a circular cross-section, although other shapes are within the scope of the present invention. FIG. 4 illustrates that the offset beam 108 may comprise a rectangular cross section, wherein such cross section provides for a low profile configuration. However, the cross section of the offset beam 108 may take on a circular shape or other desired shape to step over or around the existing screw head and associated connector. FIG. 5 shows a cross section of the transition section 140 between the rod portion 104 and the offset beam 108.

Figure 6:
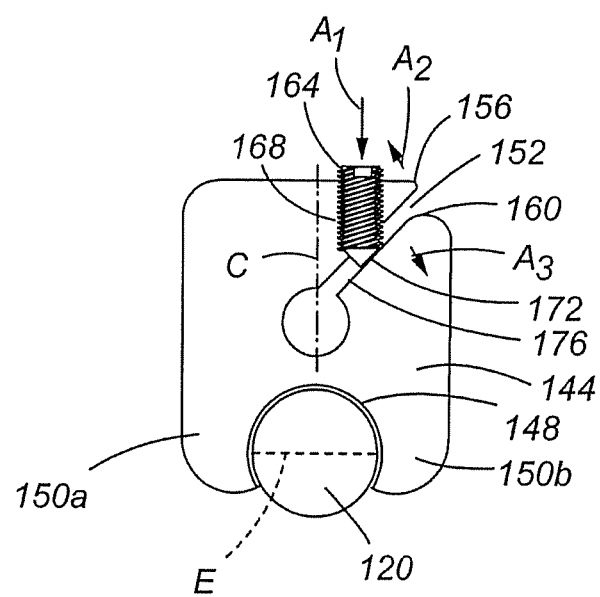
FIG. 6 is a cross-sectional view of a clamp portion of the embodiment of the present invention shown in FIG. 2.

Referring now to FIG. 6, a cross-sectional view through the clamp portion 112 of the rod extension 100 is shown. In accordance with embodiments of the present invention, the clamp portion 112 comprises a deformable body 144 having a receptacle 148 for receiving a portion of the existing rod 120, such as a portion of the existing rod 120 located between two existing pedicle screws 124. The receptacle 148 of the deformable body 144 preferably comprises opposing arms 150a and 150b, where each of the opposing arms 150a and 150b preferably extend beyond an equator E of the existing rod 120.

Referring still to FIG. 6, the deformable body 144 further includes a means for deforming the deformable body 144. As shown in FIG. 6, and in accordance with embodiments of the present invention, the means for deforming comprises a slot 152 within the body 144. The slot 152 separates a first wing 156 of the deformable body 144 from a second wing 160 of the deformable body 144, and allows the two wings 156 and 160 to be displaced relative to each other. As shown in FIG. 6, the means for deforming also comprises a screw 164 for advancement through screw hole 168. As the screw 164 is advanced in the direction of arrow A1 into screw hole 168, the distal end 172 of the screw 164 contacts shoulder 176 of second wing 160. This causes the first wing 156 to separate from the second wing 160. That is, at slot 152, first wing 156 generally moves in the direction of arrow A2, and second wing 160 generally moves in the direction of arrow A3. In turn, the opposing arms 150a and 150b of the deformable body 144 close to pinch or clamp around the existing rod 120. In order to provide sufficient leverage for the screw 164 to separate the two wings 156 and 160, the screw hole 168 is offset from the centerline C of the deformable body 144.

In accordance with embodiments of the present invention, the pedicle screws 124 and 132, and connectors 128 and 136 may allow for angular adjustment of the components. Furthermore, a variety of anchor devices, pedicle screws, connectors, and rods may be used with the present invention. U.S. Pat. No. 6,736,816 and U.S. Patent Publication Nos. US 2003-0093078; US 2003-0171751; US 2003-0191470; US 2004-0002708; and US 2004-0181223 are incorporated herein by reference in their entirety.

In a separate aspect of the invention, a method of using the rod extension 100 is provided. In accordance with embodiments of the present invention, the method comprises forming an incision in the patient, the incision not extending the entire length of an existing fusion implant 116 in the patient. Alternatively, the incision could be at least the entire length of the existing implant 116. The surgeon then installs a new pedicle screw 132 into a vertebra beyond the existing fusion implant 116. The rod extension 100 is then loosely interconnected to the newly installed pedicle screw 132, such as by inserting the rod portion 104 of the rod extension 100 into a new connector 136 that is connected to the new pedicle screw 132. The surgeon then adjusts the position of the rod extension 100, including inserting the existing rod 120 into the receptacle 148 of the clamp portion 112 of the rod extension 100. In accordance with the embodiment shown in FIGS. 1-6, the surgeon may adjust the orientation of the rod extension 100 by rotating the device, if so desired. That is, an appropriately shaped rod portion 104 and receptacle 148 for the existing rod 120 can allow at least some rotation of the rod extension 100 before tightening the rod extension 100 to the new pedicle screw 132 and existing rod 120. After properly adjusting the position of the rod extension 100, the surgeon can then advance screw 164 of clamp portion 112 to deform the deformable body 144 and secure the existing rod 120 between the opposing arms 150a and 150b of the deformable body 144.

While particular embodiments of the present invention have been described in some detail, it should be understood that other related embodiments are intended to be within the scope of the present invention. For example, other ways to functionally and structurally connect or operatively associate a supplemental rod structure with an existing implant are encompassed by the present invention, whether such structures employ clamping members that are deformable, interlocking or mating members, or other suitable connection means that are well within the knowledge of those of ordinary skill in this art, be they conventional structures or those that may be developed in the future. In particular, however, other clamping devices that provide an attachment between an existing spinal implant and an extension to the existing implant are considered within the scope of the invention. More particularly, such devices may include the use of hooks, bolts, adhesives, clamps or alternative orientations of the elements of the present invention to achieve the desired structural relationship between the existing spinal implant and a supplemental rod structure.

The present invention, in various embodiments, includes components, methods, processes, systems and/or apparatus substantially as depicted and described herein, including various embodiments, subcombinations, and subsets thereof. Those of skill in the art will understand how to make and use the present invention after understanding the present disclosure. The present invention, in various embodiments, includes providing devices and processes in the absence of items not depicted and/or described herein or in various embodiments hereof, including in the absence of such items as may have been used in previous devices or processes, e.g., for improving performance, achieving ease and/or reducing cost of implementation.

The foregoing discussion of the invention has been presented for purposes of illustration and description. Any reference to "the invention" is not intended to limit the scope of the claims in any manner, but rather is intended to denote one or more possible embodiments of the claimed invention. The foregoing is not intended to limit the invention to the form or forms disclosed herein. In the foregoing Detailed Description, for example, various features of the invention are grouped together in one or more embodiments for the purpose of streamlining the disclosure. This method of disclosure is not to be interpreted as reflecting an intention that the claimed invention requires more features than are expressly recited in each claim. Rather, as the following claims reflect, inventive aspects lie in less than all features of a single foregoing disclosed embodiment. Thus, the following claims are hereby incorporated into this Detailed Description, with each claim standing on its own as a separate preferred embodiment of the invention.

Moreover, though the description of the invention has included description of one or more embodiments and certain variations and modifications, other variations and modifications are within the scope of the invention, e.g., as may be within the skill and knowledge of those in the art, after understanding the present disclosure. It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. A method for extending an existing implant connected to at least two vertebra of a patient to a third vertebra of the patient, the existing implant including at least one or more existing pedicle screws each defining a pedicle screw long axis, at least one existing rod oriented in a cephalad-caudad orientation, and one or more existing connectors interconnecting the one or more existing pedicle screws to the at least one existing rod, wherein a spinal anchor and a connector are associated with the third vertebra, the method comprising:
    attaching a spinal rod extension to the at least one existing rod using a securing mechanism by causing the securing mechanism to grasp an exterior of the least one existing rod at a location longitudinally spaced apart from each of the one or more existing pedicle screws and the one or more existing connectors such that the spinal rod extension intersects one of the pedicle screw long axes; and
    interconnecting the spinal anchor to the spinal rod extension using the connector;
    wherein at least a portion of the spinal rod extension is adapted to be at least one of (a) oriented substantially aligned with the at least one existing rod or (b) oriented aligned substantially parallel to the at least one existing rod.

2. The method of claim 1, wherein using the securing mechanism includes advancing a screw.

3. The method of claim 1, wherein the securing mechanism comprises a clamp that includes a first wing and a second wing, and wherein attaching the spinal rod extension to the at least one existing rod using the securing mechanism includes advancing a screw through a screw hole and through a portion of a slot into contact with the second wing of the clamp to achieve a separation of the first wing from the second wing, wherein the separation results in securing the securing mechanism to the existing rod.

4. The method of claim 1, further comprising forming an incision in the patient, inserting the anchor portion through the incision and installing the anchor portion in the third vertebra.

5. The method of claim 4, wherein the incision extends less than an entire length of the existing implant.

6. The method of claim 4, wherein the incision extends at least an entire length of the existing implant.

7. The method of claim 1, wherein interconnecting the spinal anchor to the spinal rod extension comprises inserting a rod portion of the spinal rod extension into a cavity of the connector.

8. The method of claim 1, wherein attaching the spinal extension rod to the at least one existing rod comprises inserting the at least one existing rod into a receptacle of the securing mechanism.

9. The method of claim 8, wherein:
the receptacle includes an opening defined by a distance between opposing arms of the securing mechanism; and
the securing mechanism is movable between a first position in which the opening has a maximum width that is greater than that of the at least one existing rod and the at least one existing rod is movable within the receptacle and a second position in which the maximum width of the opening is less than that of the at least one existing rod.

10. The method of claim 8, wherein:
the receptacle includes an opening defined by a distance between opposing arms of the securing mechanism; and
the securing mechanism is deformable to move the securing mechanism between a first position in which the opening has a maximum width that is greater than that of the at least one existing rod and the at least one existing rod is movable within the receptacle and a second position in which the maximum width of the opening is less than that of the at least one existing rod.

11. The method of claim 10, wherein each of the opposing arms extends beyond an equator of the at least one existing rod that bisects the at least one existing rod in a direction that is perpendicular to a longitudinal axis defined by the at least one existing rod.

12. The method of claim 1, wherein the spinal rod extension includes a rod portion that extends parallel to the at least one existing rod.

13. The method of claim 1, wherein the spinal rod extension includes a rod portion that extends transverse to the at least one existing rod.

14. The method of claim 1, wherein inner surfaces of each of the one or more existing connectors engage an outer surface of the at least one existing rod to couple the at least one existing rod to the one or more connectors.

15. The method of claim 1, further comprising rotating the spinal rod extension relative to the at least one existing rod to adjust an orientation of spinal rod extension about a long axis of the at least one existing rod.

16. The method of claim 1, wherein the at least one existing rod has a uniform cylindrical cross-sectional configuration.

17. The method of claim 1, wherein the at least one existing rod has a uniform cylindrical cross-sectional configuration and is free of any openings.

18. The method of claim 1, wherein the at least one existing rod is monolithic and extends along an existing rod long axis, a first portion of the spinal rod extension being coaxial with the existing rod long axis and a second portion of the spinal rod extension being offset from the existing rod long axis.

19. A method for extending an existing implant connected to at least two vertebra of a patient to a third vertebra of the patient, the existing implant including at least one or more existing pedicle screws, at least one existing rod oriented in a cephalad-caudad orientation, and one or more existing connectors interconnecting the one or more existing pedicle screws to the at least one existing rod, wherein a spinal anchor and a connector are associated with the third vertebra, the method comprising:
attaching a spinal rod extension to the at least one existing rod using a securing mechanism by causing the securing mechanism to grasp an exterior of the least one existing rod at a location longitudinally spaced apart from each of the one or more existing pedicle screws and the one or more existing connectors, the spinal rod extension including a rod portion that is coaxial with the at least one existing rod; and
interconnecting the spinal anchor to the spinal rod extension using the connector,
wherein the spinal rod extension includes an offset beam that extends parallel to the rod portion and is non-coaxial with the rod portion, the offset beam extending over one of the one or more existing pedicle screws and one of the one or more existing connectors, and
wherein at least a portion of the spinal rod extension is adapted to be at least one of (a) oriented substantially aligned with the at least one existing rod or (b) oriented aligned substantially parallel to the at least one existing rod.

20. The method of claim 19, wherein the rod portion has a circular cross sectional configuration and the offset beam has a rectangular cross sectional configuration to provide the offset beam with a low profile.

* * * * *

UNITED STATES PATENT AND TRADEMARK OFFICE
CERTIFICATE OF CORRECTION

PATENT NO. : 8,845,694 B2
APPLICATION NO. : 13/236200
DATED : September 30, 2014
INVENTOR(S) : Ritland It is certified that error appears in the above-identified patent and that said Letters Patent is hereby corrected as shown below:

On Title Page 5, Item (56), under "OTHER PUBLICATIONS", in Column 1, Lines 27-32, delete "Green, "Effects of Gamma Sterilisation on Implant Grade Polyetheretherketone," Invibio Inc, Lancashire, United Kingdom, undated, 1 page.
Green, "In Vivo Biostability Study on Polyaryletheretherketone Biomaterial," Invibio Inc Lancashire, United Kingdom, undated, 2 pages.".

On Title Page 5, Item (56), under "OTHER PUBLICATIONS", in Columns 1 & 2, Lines 35-37 & 1-3, delete "Green, et al. "Polyetheretherketone Polymer and Compounds for Surgical Applications," Lancashire, United Kingdom, undated, 9 pages.
Green, Stuart, "Peek-Optima Polymer in the Implantable Medical Device Industry," Invibio Inc Lancashire, United Kingdom, undated, 2 pages.".

On Title Page 5, Item (56), under "OTHER PUBLICATIONS", in Column 2, Line 4, delete ""Meditronic" and insert -- "Medtronic --, therefor.

On Title Page 5, Item (56), under "OTHER PUBLICATIONS", in Column 2, Lines 6-11, delete "Invibio, Biomaterials Solutions, "High Performance PEEK-Optima Biocompatible Polymer Chosen for Dental Abutment Healing Caps," Invibio Inc Lancashire, United Kingdom, undated, 1 page.
Invibio, Biomaterials Solutions, "High Performance PEEK-Optima Biocompatible Polymer Chosen for New Generation Heart Valve," Invibio Inc., Lancashire, United Kingdom, undated, 1 page.".

On Title Page 5, Item (56), under "OTHER PUBLICATIONS", in Column 2, Lines 17-20, delete "Invibio, Biomaterials Solutions, "PEEK-Optima, Composite Hip," Invibio Inc., Lancashire, United Kingdom, undated, 2 pages.
Invibio, Biomaterials Solutions, "Peek-Optima, Spiked Washers," Invibio Inc., Lancashire, United Kingdom, undated, 1 page.".

On Title Page 5, Item (56), under "OTHER PUBLICATIONS", in Column 2, Line 22, delete "Ubrary" and insert -- Library --, therefor.

Signed and Sealed this
Third Day of March, 2015

Michelle K. Lee
*Deputy Director of the United States Patent and Trademark Office*

CERTIFICATE OF CORRECTION (continued)
U.S. Pat. No. 8,845,694 B2

On Title Page 5, Item (56), under "OTHER PUBLICATIONS", in Column 2, Lines 23-24, delete "Kambin; "Percutaneous Posterolateral Discectomy"; Clincial Orthopaedics and Related Research. Section II; 145-154119.".

On Title Page 5, Item (56), under "OTHER PUBLICATIONS", in Column 2, Line 25, delete "Latera-Approach" and insert -- Lateral-Approach --, therefor.

On Title Page 5, Item (56), under "OTHER PUBLICATIONS", in Column 2, Lines 31-33, delete "Sofamor Danek Video Systems Brochure. "New Minimally Invasive Techniques, Improve Outcome of Spine Surgeries", Medtronic Sofamor Danek.".

On Title Page 5, Item (56), under "OTHER PUBLICATIONS", in Column 2, Line 35, delete "Keotone-PEEK,"" and insert -- Ketone-PEEK," --, therefor.

In the Specification

In Column 4, Line 13, delete "connector 112." and insert -- connector 128. --, therefor.